US 006750064B2

(12) United States Patent
Stahly et al.

(10) Patent No.: US 6,750,064 B2
(45) Date of Patent: Jun. 15, 2004

(54) METHODS OF SCREENING FOR POSSIBLE SOLID FORMS

(75) Inventors: G. Patrick Stahly, West Lafayette, IN (US); Kenneth R. Morris, West Lafayette, IN (US); Barbara C. Stahly, West Lafayette, IN (US); David Coates, West Lafayette, IN (US)

(73) Assignees: S.S.C.I. Inc., West Lafayette, IN (US); Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/752,857

(22) Filed: Dec. 28, 2000

(65) Prior Publication Data

US 2003/0190758 A1 Oct. 9, 2003

(51) Int. Cl.⁷ ................................. G01N 1/22
(52) U.S. Cl. ..................... 436/181; 436/174; 436/180
(58) Field of Search ............................ 436/180, 181, 436/174; 422/243, 245.1, 255, 258, 260

(56) References Cited

U.S. PATENT DOCUMENTS

| | | | | |
|---|---|---|---|---|
| 4,060,646 A | * | 11/1977 | Bringi et al. | 426/607 |
| 4,290,835 A | | 9/1981 | Yates et al. | 156/601 |
| 4,295,857 A | | 10/1981 | Schuler et al. | 23/301 |
| 5,009,861 A | * | 4/1991 | Plaas-Link | 117/223 |
| 5,200,910 A | * | 4/1993 | Subbiah | 702/28 |
| 5,363,797 A | | 11/1994 | Uenishi et al. | 117/68 |
| 5,614,726 A | * | 3/1997 | Kaye et al. | 204/452 |
| 5,997,636 A | | 12/1999 | Gamarnik et al. | 117/70 |
| 6,150,380 A | * | 11/2000 | Lovqvist et al. | 514/338 |
| 6,267,935 B1 | * | 7/2001 | Hol et al. | 422/245.1 |
| 6,371,640 B1 | | 4/2002 | Hajduk et al. | 378/208 |
| 6,507,636 B1 | * | 1/2003 | Lehmann | 378/79 |
| 2002/0048610 A1 | | 4/2002 | Cima et al. | 424/725 |

FOREIGN PATENT DOCUMENTS

JP            06095190 A    *   4/1994

OTHER PUBLICATIONS

Chyall et al. "Polymorph Generation in Capillary Spaces...", Crystal Growth and Design, 2002, v. 2, No. 6, pp. 505–510.*
Kajola "Syntheses in capillary tubes" Acta Chem. Scand. (1954), 8, 698–9 (Abstract).*
Stephenson, et al., "Solid–State Analysis of Polymorpnic, Isomorphic, and Solvated Forms of Dirithromycin," *Journal of American Chemical Society*, 116, pp. 5766–5773, 1994.
Bryn et al., "Solid–State Chemistry of Drugs," *SSCI, Inc.*, Second Edition, pp. 1–574, 1999.
Giordano, et al., "Crystal Forms of Piroxicam Pivalate: Preparation and Characterization of Two Polymorphs," *Journal of Pharmaceutical Sciences*, vol. 87, No. 3, pp. 333–346, Mar. 1998.

Bartolomei, et al., "Solid–State Investigation of Fluocinolone Acetonide," *Journal of Pharmaceutical and Biomedical Analysis*, 15, pp. 1813–1820, 1997.
Kiss, et al., "Solid State Investigation of Mefloquine Hydrochloride," *Journal of Pharmaceutical & Biomedical Analysis*, vol. 12, No. 7, pp. 889–893, 1994.
Caira, et al., "Structure and Thermal Stability of Alprazolam and Selected Solvates," *Journal of Pharmaceutical Sciences*, vol. 84, No. 11, pp. 1379–1384, Nov. 1995.
Wu, et al., "Investigation of Moricizine Hydrochloride Polymorphs," *Journal of Pharmaceutical Sciences*, vol. 83, No. 10, pp. 1404–1406, Oct. 1994.
Hildebrand, et al., "Ketoprofen Sodium: Preparation and Its Formation of Mixed Crystals with Ketoprofen," *Journal of Pharmaceutical Sciences*, vol. 86, No. 7, 854–857, Jul. 1997.
Agafonov, et al., "Polymorphism of Spironolactone," *Journal of Pharmaceutical Sciences*, vol. 80, No. 2, pp. 181–185, Feb. 1991.
Singh, et al., "Solid–State Characterization of Chlordiazepoxide Polymorphs," *Journal Pharmaceutical Sciences*, vol. 87, No. 5, p. 655, May 1998.
Chang, et al., "Solid State Characterization of Dehydroepiandrosterone," *Journal of Pharmaceutical Sciences*, vol. 84, No. 10, pp. 1169–1179, Oct. 1995.
Tros de Ilarduya, et al., "Polymorphism of Sulindac: Isolation and Characterization of a New Polymorph and Three New Solvates," *Journal of Pharmaceutical Sciences*, vol. 86, No. 2, pp. 248–251, Feb. 1997.
Beckmann, "Seeding the Desired Polymorph: Background, Possibilities, Limitations, and Case Studies," *Organic Process Research & Development*, vol. 4, pp. 372–383, 2000.
Threfall, "Crystallization of Polymorphs: Thermodynamic Insight into the Role of Solvent," *Organic Process Research & Development*, 4, pp. 384–390, 2000.
Vrcelj, et al., "Polymorphism in 2,4,6–Trinitrotoluene Crystallized from Solution," *Journal of American Chemical Society*, 123, pp. 2291–2295, 2001.
Caira, et al., "Structural Characterization of Two Polymorphic Forms of Piroxicam Pivalate," *Journal of Pharmaceutical Science*, vol. 87, No. 12, pp. 1608–1614, Dec. 1998.

(List continued on next page.)

*Primary Examiner*—Yelena G. Gakh
(74) *Attorney, Agent, or Firm*—McAndrews, Held & Malloy, Ltd.

(57) ABSTRACT

Methods for searching for possible forms of a sample and methods of screening a sample according to its form comprise disposing the sample in at least one receptacle that defines a capillary space, such as a capillary tube. The sample is solidified to generate at least one solid form or semisolid form, and the generated form is analyzed and classified. The analysis may determine differences in molecular arrangement of the various forms or characteristics that reflect the form. The methods may employ a plurality of samples, conditions, or receptacles in an effort to generate a variety of forms, so that all or a high percentage of possible forms are obtained.

10 Claims, No Drawings-

OTHER PUBLICATIONS

Gu, et al., "Characterization of Polymorphic Forms of Fluconazole Using Fourier Transform Raman Spectroscopy," *Journal of Pharmaceutical Sciences*, vol. 84, No. 12, pp. 1438–1441, Dec. 1995.

Salem, et al., "Preparation, Characterization and Transformation of Terfenadine Polymorphic Forms," *International Journal of Pharmaceutics*, 141, pp. 257–259, 1996.

Hassan, et al., "Characterization of Famotidine Polymorphic Forms," *International Journal of Pharmaceutics*, 149, pp. 227–232, 1997.

Ghodbane, et al., "Study of the polymorphism of 3-(((3-(2-(7-chloro-2-quinolinyl)-(E)-ethenyl)phenyl)((3-(3-(dimethylamino-3-oxopropyl)thio)methyl)-thio)propanoic acid (MK571) by DSC, TG, XRPD and Solubility Measurements," *International Journal of Pharamceutics*, 59, pp. 281–286, 1990.

Pienaar, et al., "Polymorphs of Nitrofurantoin. 2. Preparation and X-ray Crystal Structures of Two Anhydrous Forms of Nitrofurantoin," *Journal of Crystallographic and Spectroscopic Research*, vol. 23, No. 10, 785–790, 1993.

Chao, et al., "Polymorphism of 1,2-Dihydro-6-neopentyl-2-oxonicotinic Acid: Characterization, Interconversion, and Quantitation," *Pharmaceutical Research*, vol. 4, No. 5, pp. 429–432, 1987.

Gavezzotti, et al., "Polymorphic Forms of Organic Crystals at Room Conditions: Thermodynamic and Structural Implications," *Journal of American Chemical Society*, 117, pp. 12299–12305, 1995.

Henck, et al., "Polymorphism of Tedisamil Dihydrochloride," *Journal of Pharmaceutical Sciences*, vol. 89, No. 9, pp. 1151–1159, Sep. 2000.

Nomura, et al., "Thermal Polymorphic Transformation of p–tert–Butylcalix[4]arene Derivatives Bearing Amino Acid Substituents," *Journal of Organic Chemistry*, vol. 65, No. 19, pp. 5932–5936, 2000.

Gavezzotti, "A Molecular Dynamics Test of the Different Stability of Crystal Polymorphs under Thermal Strain," *Journal of American Chemical Society*, 122, pp. 10724–10725, 2000.

Dinnebier, et al., "Structural Characterization of Three Crystalline Modifications of Telmisartan by Single Crystal and High–Resolution X–ray Powder Diffraction," *Journal of Pharmaceutical Sciences*, vol. 89, No. 11, pp. 1465–1479, Nov. 2000.

Henck, et al., "Disappearing and Reappearing Polymorphs. The Benzocaine:Picric Acid System," *Jouranl of American Chemical Society*, 123, pp. 1834–1841, 2001.

Threlfall, "Analysis of Organic Polymorphs, A Review," *Analyst*, 120, pp. 2435–2448, Oct. 1995.

Spruijtenburg, "Examples of the Selective Preparation of a Desired Crystal Modification by an Appropriate Choice of Operating Parameters," *Organic Process Research & Development*, 4, pp. 403–406, 2000.

Beckmann, et al., "Occurrence, Stability, Kinetics of Crystallization and Polymorphic Transition of the A, B and C Modification of Abecarnil, Influence of Supersaturation, Temperature, Solvents and Impurities," *Institution of Chemical Engineers Trans IChemE*, vol. 74, Part A, pp. 750–758, Oct. 1996.

Yu, et al., "Thermochemistry and Conformational Polymorphism of a Hexamorphic Crystal System," *Journal of American Chemical Society*, 122, No. 4, pp. 585–591, 2000.

Stephenson et al., "Conformational and Color Polymorphism of 5–Methyl–2–[(2–nitrophenyl)amino]–3–thiophenecarbonitrile," *Journal of Pharmaceutical Sciences*, vol. 84, No. 11, pp. 1385–1386, Nov. 1995.

Moore, et al., "Crystal and Molecular Structures of Two Polymorphs of 4–Methyl–2–Nitroacetanilide (MNA)," *Journal of Crystallographic and Spectroscopic Research*, vol. 13, No. 4, pp. 279–292, 1983.

Moore, et al., "Crystal and Molecular Structure of an Amber Polymorph of 4–Methyl–2–Nitroacetanilide (MNA)," *Journal of Crystallographic and Spectroscopic Research*, vol. 14, No. 3, pp. 283–291, 1983.

Singh, et al., "Solid–State Characterization of Chlordiazepoxide Polymorphs," *Journal of Pharmaceutical Sciences*, vol. 87, No. 5, pp. 655–662, May 1998.

Harris, et al., "'Polymorphism' in a Novel Anti–Viral Agent: Lamivudine," *Journal of Chemical Society, Perkin Trans.*, 2, pp. 2653–2659, 1997.

Caira, et al., "Crystal and Molecular Structures of Three Modifications of the Androgen Dehydroepiandrosterone (DHEA)," *Journal of Chemical Crystallography*, vol. 25, No. 7, pp. 393–400, 1995.

Cox, et al., "Structure of 3β–Hydroxy–5–androsten–17–one (DHEA) Monohydrate," *International Union of Crystallography*, pp. 334–336, 1990.

Swanson, et al., "Model of the Evaporating Mensicus in a Capillary Tube," *Transactions of the ASME, Journal of Heat Transfer*, vol. 114, pp. 434–441, May 1992.

Stewart, et al., "The Formation of Particle Clusters Near An Interfacial Meniscus," *Chemical Engineering Science*, vol. 48, No. 4, pp. vol. 771–788, 1993.

Laurindo, et al., "Evaporation in Capillary Porous Media. An Experimental and Numerical Network Study," *Proceedings of the ASME Heat Transfer and Fluids Engineering Divisions*, HTD–vol. 321, FED–vol. 233, pp. 637–649, 1995.

Khrustalev, et al., "Fluid Flow Effects in Evaporation From Liquid–Vapor Meniscus," *Transactions of the ASME, Journal of Heat Transfer*, vol. 118, pp. 725–730, Aug. 1996.

Kuz, "Model for the Convective Transport of Particles in a Two–Dimensional Cluster," *American Chemical Society*, Langmuir, 13, pp. 3900–3901, 1997.

Douglas, et al., "Wetting of a Chemically Heterogeneous Surface," *Journal of Chemical Physics*, vol. 110, No. 12, pp. 5969–5977, Mar. 22, 1999.

Amaro–Gonzalez, et al., "Gas antisolvent crystallization of organic salts from aqueous solutions," *The Journal of Supercritical Fluids*, 17, pp. 249–258 (2000).

Mullin, "Crystallization Techniques and Equipment," *Crystallization*, Butterworth–Heinemann, pp. 265–368, 1993.

Guillory, "Generation of Polymorphs, Hydrates, Solvates, and Amorphous Solids," *Polymorphism in Pharmaceutical Solids*, pp. 183–226, Marcel–Dekker, Inc. 1999.

He, et al., "Conformational Color Polymorphism and Control of Crystallization of 5–Methyl–2–[(4–methyl–2–nitrophenyl)amino]–3–thiophenecarbonitrile," *Journal of Pharmaceutical Sciences*, vol. 90, No. 3, pp. 371–388, Mar. 2001.

Cristian, et al., "The Mechanism of Material Drying v. Liquid Evaporation From Capilaries," *Buletinul Institutului Politehnic Din Iasi, Sectia II*, pp. 37–43, 1979.

Overman, et al., "Convective Diffusion in Capillaries," *The Journal of Physical Chemistry*, vol. 72, No. 1, pp. 155–158, Jan. 1968.

Preiss, et al., "Evaporation From A Capillary Tube," *Transactions of the ASME, Journal of Heat Transfer*, pp. 178–181, May 1976.

Christenson, et al., "Growth of Ionic Crystallites on Exposed Surfaces," *Journal of Colloid and Interface Science*, vol. 117, No. 2, pp. 576–577, Jun. 1987.

Sibille, et al., "Analysis of solvent evaporation rates in the vapor diffusion protein crystal growth experiments from STS–61C Space Shuttle Mission," *Journal of Crystal Growth*, 110, pp. 72–79, 1991.

Sibille, et al., "Solvent evaporation rates in the enclosed capillary vapor diffusion method of protein crystal growth," *Journal of Crystal Growth*, 110, pp. 80–88, 1991.

* cited by examiner

METHODS OF SCREENING FOR POSSIBLE SOLID FORMS

FIELD OF THE INVENTION

The present methods relate to screening for possible solid forms of a sample and include solidifying the sample in at least on receptacle defining a capillary space, such as a capillary tube of well plate. The present methods also relate to screening a sample according to its solid forms and include solidifying the sample in a plurality of receptables and at least one receptacle defines a capillary space. The solid for of the sample refers to its arrangement at the molecular or atomic level in the solid. The solid forms generated by the solidification step are analyzed and classified, such as by x-ray diffraction patterns. The present methods increase the likelihood of generating all or a high percentage of possible solid forms.

BACKGROUND OF THE INVENTION

In the chemical field, the unpredictability and variability of compounds, mixtures, and processes are well established. Certain chemical compounds or mixtures may have utility for numerous different applications, including vital biological applications, yet a slight change in those compounds or mixtures, even with respect to a single atom, may reduce or eliminate their utility for their beneficial purpose. Similarly, certain chemical processes may have significantly better or worse performance based upon seemingly minor differences.

In the pharmaceutical field, a great deal of time, effort and expense is spent on the identification of particular compounds and mixtures that will have beneficial effect. Furthermore, exhaustive research must be done as to whether such compounds and mixtures will have harmful effects. Once again, even slight differences in chemical composition or structure may yield significant differences in biological activity. Thus, researchers frequently test many different compounds and mixtures for biological activity and other effects as well as testing different processes and conditions for the preparation of such chemical compounds and mixtures.

The process of thorough analysis of different chemical compounds, elements, mixtures, processes, or structures is commonly referred to as screening. Screening may be a function of time and effort, with the quality or results of screening being a function of the number of samples prepared and/or analyzed as well as the quality of preparation and/or analysis underlying those samples. Screening plays a vital role in the pharmaceutical field, as the most advantageous formulation of a biologically active compound or mixture is frequently found through successful screening processes.

However, screening processes can require significant amounts of time, effort and resources. There is a continuous need for improved screening processes having increased reliability and efficiency.

Processes have been used for screening chemical compounds according to their form. When a compound has different solid or crystalline forms, the different forms are frequently referred to as polymorphs of the compound. A "polymorphic" compound as used herein means a compound having more than one solid form. For example, a polymorphic compound may have different forms of its crystalline structure, or different forms based upon hydration, or it may have a crystalline form and an amorphous form. In the past, screening processes have not identified with sufficient consistency and reliability a high percentage of possible solid and semisolid forms.

The form of a compound or mixture may have an impact on biological activity. The same chemical compound may exhibit different properties depending upon which form (such as amorphous or crystalline or semisolid) that compound is in. A "semisolid" form is used herein to indicate materials like waxes, suspensions, gels, creams, and ointments. The term "solid form" herein includes semisolid forms. Furthermore, a chemical compound may exist in different solid forms, and those different solid forms may also exhibit different properties. As a result, different solid forms, including different crystalline forms, of a chemical compound may have greater or lesser efficacy for a particular application. The identification of an optimal solid form is important in the pharmaceutical field, as well as in other fields including nutraceuticals, agricultural chemicals, dyes, explosives, polymer additives, lubricant additives, photographic chemicals, and structural and electronic materials. The new methods described herein may be useful in any of these fields as well as others where solid materials are used.

A chemical compound or mixture may be amorphous, meaning that it is not characterized by a regular arrangement of molecules. Alternatively (or even to a limited extent within a mostly amorphous form), a compound or mixture may be arranged in a crystalline state, where the molecules exist in fixed conformations and are arranged in a regular way. The same compound or mixture may exhibit different properties depending upon which solid form that compound or mixture is in.

It is important in the pharmaceutical field as well as other fields to find the form of a chemical compound that exhibits appropriate physical and chemical properties. One form may be more stable or have other properties that make it preferable over other forms. One form of a chemical composition may have better bioavailabilty, solubility, or adsorption characteristics or in other ways be more suitable for delivery of therapeutic doses than other forms. As part of a screening method, it may be advisable to evaluate different salts of a chemical compound (or more precisely, different salt compounds of a given biologically active ion). It is frequently desirable within a screening process to generate, or at least search for, a high percentage of the possible solid forms of a compound or mixture. Past attempts to generate a variety of solid forms involved flash evaporations, cooling under different conditions and/or the addition of seeds of solid material. However, some materials strongly resist the generation of new solid forms.

One or more solid forms may be generated by crystallization of the sample. Among the phenomena in crystallization are nucleation and growth. Crystal nucleation is the formation of an ordered solid phase from liquids, supersaturated solutions, saturated vapors, or amorphous phases.

Nucleation may be achieved by homogeneous or heterogeneous mechanisms. In heterogeneous mechanisms, some solid particle is present to provide a catalytic effect and reduce the energy barrier to formation of a new phase. Crystals may originate on a minute trace of a foreign substance (either impurities or container walls) acting as a nucleation site. Since nucleation may set the character of the crystallization process, the identity of the foreign substance is an important parameter. The presence of "seeds" of other crystalline compounds in a crystallization environment can be beneficial, detrimental, or both, but in any event, must be considered. Growth is the enlargement of crystals caused by deposition of molecules on an existing surface. In homogeneous mechanisms, it has been theorized by others that nucleation is achieved spontaneously with the solution comprising the solute to be crystallized in solvent typically by evaporation, temperature reduction, or addition of antisolvent.

Typically, a solid to be crystallized is present in a solution at, above, or below its saturation point at a given temperature. Crystallization is initiated or facilitated by removing solvent, changing temperature, and/or adding an antisolvent. The solvent may be removed by evaporation or other means. Eventually the solution reaches a point where crystals will grow.

A specific chemical substance may crystallize into different forms or transition from one polymorph form, pseudopolymorph form, or amorphous form to another form. This crystallization into a different form or transition into a different form may be accompanied by other physical or chemical changes. For example, novobiocin has at least two different forms: an amorphous form and a crystalline form. Dog plasma levels of novobiocin vary depending on which form of novobiocin is administered. In one study, two hours after the amorphous form of the drug was administered, the concentration of novobiocin was 29.3 mg/mL. In contrast, when crystalline novobiocin was administered, there was no drug detectable in the dog plasma two hours after the drug was administered. In another example, furosemide has two different crystalline forms, and furosemide solubility in aqueous buffer at pH 3.2 varied depending on which polymorph was studied. After three hours, Form I and Form II had solubilities of approximately 0.025 mg/mL. Under the same conditions and dissolution time, the DMF and dioxane solvates of furosemide had solubilities of approximately 0.035, and Form III had a solubility of approximately 0.045 g/mL.

It is known to generate crystalline samples in capillary tubes. For example, U.S. Pat. No. 5,997,636 discusses a method for growing crystals within a capillary tube. As another example, D. Amaro-González et al., "Gas Antisolvent Crystallization Of Organic Salts From Aqueous Solution", Journal Of Supercritical Fluids, 17 (2000) 249–258, discloses results of crystallization of lobenzarit, including crystallizations in capillaries. Lobenzarit is an anti-arthritic agent. Amaro-González et al. state that particle size and agglomeration varied depending on the size of the capillary, that it is shown that the size distribution and particle shape can be controlled using different capillary diameters, and that it is possible to obtain individual crystals without agglomeration.

Neither reference discloses that different forms (meaning different arrangements on the molecular or atomic level) were produced, nor does either reference suggest a new method for searching for possible forms or screening a sample according to its form. A different particle size or shape does not necessarily mean there is a different crystal form since a solid form can crystallize into many different shapes. For example, snowflakes may comprise a single crystal form having many different crystal shapes.

It is also known to subject samples within capillary tubes to various spectroscopic analyses, including diffraction analysis such as x-ray diffraction analysis. However, in such instances, it has been the common practice to prepare a solid sample outside the capillary tube before it is placed in the capillary tube for analysis.

There are several factors that discourage the use of capillary tubes for solidifying compounds or mixtures. One factor is that capillary tubes are more difficult to work with than other containers. Another factor is that there has been no general recognition that the use of capillary spaces may affect reactions or lead to compositional or chemical differences. Thus, since it was believed that the same forms and reactions could be done in other containers, it is believed that capillary tubes have not been used as an integral part of a screening process or to search for and generate solid and semisolid forms.

There is a need for improved screening methods that identify all or a high percentage of possible forms of a compound or mixture. There is a need for improved methods of searching for the possible forms of a sample.

SUMMARY OF THE INVENTION

As one aspect, an improved method of searching for possible forms of a sample is provided. The method comprises the steps of disposing the sample on one or more receptacles, where at least one of the receptacles defines a capillary space, and the sample is disposed within the capillary space. The method next comprises solidifying the sample in or on the receptacles to generate at least one form, wherein the generated form(s) is a solid or semisolid. The form(s) is then analyzed and classified, such as by classification according to what form it is.

As another aspect, an improved method of screening a sample according to its form is provided. This method is especially useful for screening a sample comprising a compound or a. mixture having biological activity in at least one form of the compound or mixture. The screening method comprises the steps of disposing the sample on a plurality of receptacles, where at least one of the receptacles defines a capillary space, and the sample is disposed within the capillary space. The method next comprises solidifying the sample in or on the receptacles to generate at least one form, wherein at least one form is a solid or semisolid. The method further comprises analyzing at least one form in a manner wherein the analytical result is indicative of the generated form(s), and classifying the generated form(s), such as by form type or according to analytical result.

The screening method may be particularly useful where the compound or mixture has at least one form having biological application and it is desirable to determine if other forms are possible. The present methods may comprise generating at least one other form of the compound or mixture.

The sample may comprise a known polymorphic compound or comprise at least one material that is not recognized as a polymorphic compound. The sample may consist essentially of a solution of one compound, or may comprise a mixture of compounds.

Preferably, the present methods include disposing the sample on a plurality of receptacles, including at least two different types of receptacles. For example, one portion of a sample may be disposed in a capillary tube that defines a capillary space and another portion of the sample may be disposed on a glass slide that does not define a capillary space. The sample may be prepared in a single batch or in multiple batches. After the portions have solidified, the form disposed in the capillary tube and the form disposed on the slide may be analyzed, classified and compared.

A preferred receptacle defining a capillary space is a capillary tube, and others include a well plate, a block and a sheet with holes or pores of appropriate size and shape.

The present methods may further comprise the step of comparing the generated form to a known form. In many cases, the generating step may produce at least one different form of the sample.

At least some of the receptacles may be subjected to substantially constant motion during the generating step. For example, a capillary tube may be rotated along its longitudinal axis during the generating step or subjected to centrifuging during the generating step. Centrifuging can be sufficient to concentrate the solid or semisolid at one end of a capillary tube and to facilitate in-situ analysis of the generated forms. Also, variations in centrifuging may provide environmental variation, which is desired in a screening method. Centrifuging may move the sample to the bottom of the receptacle when one end of the receptacle is closed. Centrifuging may be performed at a pressure lower than ambient pressure, or under vacuum.

In the present methods, the sample may comprise a compound comprising a biologically active ion or one or more different salts of the compound. A second analyzing step may be performed on generated forms, where the second analyzing step provides data indicative of biological activity or bioavailability.

In the present methods, the generated forms may be analyzed by any suitable means, such as methods selected from the group consisting of visual analysis, microscopic analysis, thermal analysis, diffraction analysis, and spectroscopic analysis. Preferred methods of analysis include Raman spectroscopic analysis and x-ray diffraction analysis, more preferably using synchrotron radiation as the radiation source for the analysis. The analysis may determine differences in arrangement of molecules in the solid or determine one or more other characteristics that directly or indirectly reflect the form.

In the present methods, the step of analyzing the generated form may comprise analyzing the form without removing it from the receptacle in which it was generated. Thus, the present methods are useful for in situ analysis of generated forms. The use of capillary tubes as receptacles can facilitate such in situ analysis.

It may be advantageous to place the sample in at least five receptacles defining capillary spaces, alternatively at least 100 receptacles defining capillary spaces. In some embodiments, a sample is placed in several sets of numerous capillary tubes (for example, from 5 to 2000 capillary tubes, alternatively 5 to 100 capillary tubes), and the different sets are subjected to different methods or conditions of solidification.

The solidifying step may comprise crystallizing the sample, or may be selected from the group consisting of solvent evaporation, cooling, anti-solvent addition, gel diffusion, and thin-layer deposition.

A supersaturated solution of the sample can be formed before, during, or after the sample is disposed on the receptacle(s).

The generating step preferably comprises crystallizing the sample, or alternatively is selected from the group of methods consisting of solvent evaporation, cooling, anti-solvent addition, gel diffusion, and thin-layer deposition (with or without subsequent measures to quickly remove residual solvent, including air of various temperatures forced through the capillaries).

The receptacle that defines a capillary space can be a capillary tube or appropriately sized multi-well plate. Alternatively, the receptacle that defines a capillary space may be a block or a sheet made of polymer, glass, or other material, which has holes or pores of a suitable shape and dimensions. Alternatively, some receptacles need not define a capillary space; indeed, it is considered preferable to employ different kinds of receptacles for generating solid and/or semisolid forms of a given sample. Additional receptacles may include a glass slide or a conveyer surface in addition to the receptacle(s) defining capillary spaces.

DETAILED DESCRIPTION OF PREFERRED EMBODIMENTS

The use of receptacles that define capillary spaces is an improvement over more labor-intensive methods of generating solid forms and enables one to obtain a high percentage of possible solid and semisolid forms. Another advantage of such receptacles is that smaller amounts of the compound or mixture are used. A compound is a substance composed of atoms or ions in chemical combination. A compound usually is composed of two or more elements, though as used in accordance with the present methods, a compound may be composed of one element.

A "polymorph" as used herein means a compound or mixture having more than one solid or semisolid form. The "form" of a compound or mixture refers to the arrangement of molecules in the solid. A "semisolid" form is used herein to indicate materials like waxes, suspensions, gels, creams, and ointments. The term "solid form" herein includes semisolid forms. "Capillary space" is defined herein to mean a space having walls separated by from about 0.1 mm to about 30 mm, preferably from about 0.5 mm to about 5 mm, more preferably from about 0.5 mm to about 2.5 mm, in at least one dimension. A capillary tube having an inner diameter from about 0.5 mm to about 2.5 mm , is a preferred receptacle that defines a capillary space in the interior of the capillary tube. It is preferred that the capillary tubes are circular in their interior shapes.

As used herein, the generation of solid and semisolid forms includes any suitable technique for solidification including but not limited to crystallization. Indeed, the forms which may be sought or generated may include amorphous forms, mixtures of amorphous forms, eutectic mixtures, mixed crystal forms, solid solutions, co-crystals, and other forms.

In certain embodiments of the present methods, solid samples are generated in receptacles through a suitable means of solidification. Typically, a solution containing a compound or mixture to be solidified and a solvent is placed in a receptacle defining a capillary space, such as a capillary tube. The compound or mixture can be present in a solution below, at or above its saturation point at a given temperature at the time it is placed in a capillary tube. Through evaporation, the use of an antisolvent, temperature variation, and/or other suitable means, the system reaches a point where solidification begins. After a suitable amount of time, when solid or semisolid appears, the resulting sample is ready for analysis.

Any suitable crystallization technique may be employed for obtaining crystals. For example, crystals may be obtained through cooling, heating, evaporation, addition of an antisolvent, reactive crystallization, and using supercritical fluids as solvents. Additionally, melt crystallization techniques may be used to generate a solid form. Through such techniques, the use of a solvent can be avoided. In such techniques, formation of crystalline material is from a melt of the crystallizing species rather than a solution. Additionally, the crystallization process may be done through sublimation techniques.

Crystallization may be performed as a seeded operation or an unseeded operation. In a seeded operation, a selected quantity of seed crystals is included in the system. The characteristics of the seed crystals typically influence the characteristics of the crystals generated from the system. Crystallization may be performed by heterogeneous or homogeneous mechanisms.

In other embodiments of the present methods, the form is generated other than by crystallization. The sample may be in the form of a melt that is then added to the capillary tube and allowed to solidify in an amorphous form. Alternatively, the mechanism by which solidification is accomplished may include gel diffusion methods, thin-layer deposition methods, or other suitable methods. Other thermodynamic and kinetic conditions may be employed to solidify the compound or mixture. Cooling of a saturated solution is a typical thermodynamic condition. An addition of a solution of the compound or mixture to an excess of cold anti-solvent is a typical kinetic condition.

Any material capable of forming a solid or semisolid may be used in the present methods. In particular, the present methods are especially suited for materials characterized by molecules which are associated by non-bonded interactions (e.g. van der Waals forces, hydrogen bonding, and Columbic interaction).

The present methods may be advantageously used with small organic drug molecules having solubility of at least 1 mg/mL in ethanol at ambient conditions. The present methods are also contemplated for use with large organic molecules and inorganic molecules. Examples of compounds having more than one solid form include 5-methyl-2-[(2-nitrophenyl)amino]-3-thiophenecarbonitrile and 4-methyl-2-nitroacetanilide, each of which may be different colors in connection with different forms, and novobiocin and furosemide, which are discussed above. This list cannot be exhaustive as the present methods may provide significant benefits for novel compounds and mixtures whose identities, or at least whose possible forms, are not yet identified.

The generation of a variety of forms is an important object of screening. A sufficient number of diverse processes and conditions should be employed to maximize the likelihood that a high percentage of possible solid forms of a chemical compound is generated. Samples should be generated under various thermodynamic and kinetic conditions.

It is preferable that the generation of solid and/or semisolid forms within the receptacles is carried out under a wide variety of conditions. For example, solids should be generated in the presence and absence of various solvents, as the solvent may play a role in the formation of certain forms.

As another example it is also preferable to prepare samples under different conditions of temperature and pressure, as different solid forms may be favored by different conditions.

The various forms generated may be identified by any suitable method, including but not limited to visual analysis (such as when different forms exhibit different colors), microscopic analysis including electron microscopy, thermal analysis such as determining the melting points, conducting diffraction analysis (such as x-ray diffraction analysis, electron diffraction analysis, neutron diffraction analysis, as well as others), conducting an infrared spectroscopic analysis, or conducting other spectroscopic analysis. Any appropriate analytical technique that is used to differentiate structural, energetic, or performance characteristics may be used in connection with the present methods.

The classifying step may comprise classifying the generated form(s) according to any of the analytical results, such as appearance, solubility, or x-ray diffraction pattern.

In a preferred embodiment, a synchrotron may be used as the source of radiation for conducting diffraction analyses. A synchrotron is a type of particle accelerator, which emits high energy, focused radiation. Synchrotron radiation is the byproduct of circulating electrons or positrons at speeds very close to the speed of light. Synchrotron radiation contains all the wavelengths of the electromagnetic spectrum and comprises the most intense source of wavelengths available in the x-ray and ultraviolet region. Synchrotron radiation allows analysis of smaller quantities of sample that would be difficult to analyze using other sources of x-ray radiation.

One location for research using synchrotron radiation is the Stanford Synchrotron Radiation Laboratory (SSRL), which is funded by the Department of Energy as a national user facility. Another location is Argonne National Laboratory, which is available to outside users on a fee basis.

Synchrotron radiation may be used to study structural details of solid samples with a resolution not practically attainable using traditional x-ray instrumentation. This may enable differentiation between different polymorphic forms or compounds that is not attainable with other x-ray radiation sources.

Preferably, the present methods comprise generating more than one form such that a distribution of forms is obtained.

However, by generating solid forms in receptacles defining capillary spaces, one may favor the formation of a variety of solid forms and increase the likelihood of generating all or a high percentage of possible forms.

The present methods can significantly assist in the identification of the form of a compound or a mixture that is most stable or has other properties that make it preferable over other forms. For example, the present methods can be used as part of a screening method and can improve the likelihood of identifying a form having biological activity such as better bioavailability, solubility, or adsorption characteristics. In some cases, an identified form may have better activity as an active agent.

After the sample is placed in a receptacle, the receptacle may be centrifuged. Centrifugation may be employed for a variety of reasons. First, centrifuging may assist evaporation or concentrate solid or semisolid material at one end of a capillary space. This has advantages in connection with in-situ analysis, in that the generated form will be located at a consistent place in the receptacle. Also or alternatively, centrifuging may be used to provide additional environmental variation, which is desirable in a screening method.

EXAMPLE 1

Portions of a sample of 4-(6-methoxy-2-naphthyl)-butan-2-one (Compound A) were dissolved in various solvents (acetone, acetonitrile, aqueous ethanol, ethanol, ethyl acetate, tetrahydrofuran, toluene, benzene, chloroform, methyl ethyl ketone, methanol, butyl acetate, methylene chloride, hexane, aqueous tetrahydrofuran, aqueous methanol, aqueous acetone, and aqueous acetonitrile) to make saturated solutions ranging in concentration from 5–50 mg/ml depending on the solvent. The solutions were filtered through 0.2 μm nylon syringe filters into automatic pipettes. Aliquots (ranging from 5–25 microliters) of the solutions were introduced into 40 glass capillaries (thin-walled, both ends open, half 0.7 mm inside diameter, half 1.0 mm inside diameter). For some of the capillary tubes, the original saturated solution was heated and more 4-(6-methoxy-2-naphthyl)-butan-2-one was added until the concentration was twice that of the saturation concentration. This supersaturated solution was then used.

The capillaries were rotated about their center point at room temperature and solvent was allowed to evaporate until solid or semisolid material was visible by eye.

The resulting capillaries containing solid or semisolid material were analyzed by laboratory x-ray powder diffraction in the capillary tubes without isolation of material using and INEL XRG 3000doffractometer. Analysis of the x-ray diffraction data showed two different x-ray powder patterns: the original crystalline form reported in the literature, and one new crystalline powder patterns. These two different x-ray diffraction patterns are indicative of two different solid forms. A comparative study of 4-(6-methoxy-2-naphthyl)-butan-2-one using 80 traditional screening conditions (including cyrstallization in vials, varing solvents, varying conditions including fast evaporation, slow cooling, and crash cooling) showed only the diffraction pattern of the original solid form reported in the literature.

EXAMPLE 2

Portions of a sample of sulfathiazole (compound B) are dissolved in various solvents (aqueous ethanol, acetonitrile, ethanol, methanol, aqueous methanol, methylene chloride, acetone, hexane, dioxane) to make saturated solutions ranging in concentration from 5–50 mg/ml depending on the solvent. The solutions are filtered through 0.2 $\mu$m nylon syringe filters into automatic pipettes. Aliquots (ranging from 5–25 microliters) of the solutions are introduce into 100 glass capillaries (thin-walled, single closed end, 0.7 mm inside diameter) and spun in a centrifuge to move the solution to the bottom of the capillary tube. For some of the capillary tubes, the original saturated solution is heated and more Compound B is added until the concentration is twice that of the saturation concentration. This supersaturated solution is then used.

The capillaries are placed in a variety of environments and solvent is allowed to evaporate until solid or semisolid material is visible by eye. Environments include 60° C. oven, 4° C. freezer, ambient temperature, storage with closed end up, storage with closed end down, and spinning of the capillaries.

It is expected that the resulting capillaries containing solid or semisolid material can be analyzed by laboratory x-ray powder diffraction in the capillary tubes without isolation of material using an INEL XRG 3000 diffractometer. Analysis of the x-ray diffraction data would show whether different forms were present, including forms in addition IBM to the known forms. Different x-ray diffraction patterns are indicative of different forms. A comparative study of sulfathiazole using 60 traditional screening conditions (crystallization in vials, varying conditions including fast evaporation, slow cooling, and crash cooling) would be expected to identify fewer different x-ray powder diffraction patterns.

EXAMPLE 3

Portions of a sample of a polymorphic compound (compound C) are dissolved in various solvents (aqueous ethanol, methylene chloride, ethanol, toluene, dimethylformamide, acetone, water, butanol, methanol, acetonitrile, methylethylketone, hexane, dioxane, and ethyl acetate) to make solutions ranging in concentration from 5–50 mg/ml depending on the solvent. The solutions are filtered through 0.2 $\mu$m nylon syringe filters into automatic pipettes. Aliquots (ranging from 5–25 microliters) of the solutions are introduced into 200 glass capillaries (thin-walled, single closed end, 0.7 mm inside diameter) and spun in a centrifuge to move the solution to the bottom of the capillary tube, which facilitates in situ analysis.

Aliquots (ranging from 5–25 microliters) of the solutions are also introduced into 100 double open-ended glass capillaries (thin-walled, double open ends, 1.0 mm inside diameter).

The capillaries are placed in a variety of environments and solvent is allowed to evaporate until solid or semisolid material it was visible by eye. Environments include 60° C. oven, 4° C., freezer, ambient temperature, storage with closed end up, and storage with closed end down. Some of the capillaries are stored under centrifugation at 40° C. and ambient pressure while the solvent evaporation took place. The 100 open-ended capillaries are rotated about their center point during solvent evaporation.

The resulting capillary tubes containing solid or semisolid material can be analyzed by synchrotron x-ray powder diffraction. It is expected that this in situ analysis of the x-ray diffraction data would show different patterns corresponding to different forms, and that more forms would be observed than if the forms were generated by a traditional screening method. Different x-ray diffraction patterns are indicative of different forms of the compound.

A comparative study using traditional screening techniques to prepare different forms of the same compound would be expected to identify fewer different x-ray diffraction patterns.

EXAMPLE 4

Solutions of an organic drug sample (compound D) are prepared in a similar way as those in Example 2. Aliquots (15–20 microliters each) of the various solutions are placed in two glass, thin-walled 96-well plates with well dimensions of approximately 2 mm×2 mm×8 mm. The solutions are evaporated by placing one plate in a SpeedVac centrifugal evaporator at 30° C. and 25 mm Hg vacuum and one in a SpeedVac centrifugal evaporator at 50° C. and 100 mm Hg vacuum. The different evaporation conditions provide different evaporation rates and other environmental variations. The resulting solid and semisolid residues are analyzed in situ by transmission x-ray powder diffraction. Analysis of the x-ray data would be expected to show distinct powder patterns for the different forms generated.

EXAMPLE 5

Following a procedure having the same steps as Example 1, forms are generated. After solutions in capillary tubes evaporate to leave solid or semisolid residue, the capillary tubes are cut to a 2 cm length containing the bulk of the residue and then crushed and analyzed by infrared (IR) spectroscopy. Analysis of the IR data would be expected to indicate presence of several different forms, that is, several distinguishable IR patterns. Different IR patterns are indicative of different forms.

What is claimed is:

1. A method of screening for a new crystal form of a substance, which comprises solidifying the substance in one or more capillary spaces each independently having an inside diameter from about 0.1 mm to about 5 mm to produce at least one crystal form of the substance;

analyzing the crystal form of the substance in at least one of the capillary spaces while the substance remains in the capillary space, using at least one technique chosen from microscopic analysis, thermal analysis, diffraction analysis, and spectroscopic analysis; and classifying the crystal form by comparing the analytical results of the crystal form of the substance to those of a know crystal form or forms of the substance and determining if the crystal form of the substance produced is new.

2. The method of claim 1, wherein the capillary spaces each independently have an inside diameter from about 0.5 mm to about 2.5 mm.

3. The method of claim 1, wherein the one or more capillary spaces form a well plate and wherein the crystal form of the substance is analyzed by transmission X-ray diffraction.

4. The method of claim 3, wherein the capillary spaces each independently have an inside diameter from about 0.5 mm to about 2.5 mm.

5. The method as claimed in claim 1, wherein the substance is solidified by solvent evaporation, cooling, heating, anti-solvent addition, gel diffusion or thin-layer deposition.

6. A method of screening for a new crystal form of a substance, which comprises solidifying the substance in one or more capillary tubes each independently having an inside diameter from about 0.1 mm to about 5 mm to produce at least one crystal form of the substance, analyzing the crystal form of the substance in a least one of the capillary tubes using at least one technique chosen from microscopic analysis, thermal analysis, diffraction analysis, and spectroscopic analysis; and classifying the crystal form by comparing the analytical results of the crystal form of the substance to those of a known crystal form or forms of the substance and determining if the crystal form of the substance produced is new.

7. The method as claimed in claim 6, wherein the capillary tubes each independently gave an inside diameter from about 0.5 mm to about 2.5 mm.

8. The method as claimed in claim 6, wherein the crystal form of the substance is analyzed by transmission X-ray diffraction.

9. The method as claimed in claim 8, wherein the capillary tubes each independently have an inside diameter from about 0.5 mm to about 2.5 mm.

10. The method as claimed in claim 6, wherein the substance is solidified by solvent evaporation, cooling, heating, anti-solvent addition, gel diffusion or thin layer deposition.

* * * * *